United States Patent [19]

Mishima

[11] Patent Number: 4,677,135

[45] Date of Patent: Jun. 30, 1987

[54] METHOD OF PREPARING UREA ADSORBENT

[75] Inventor: Masayuki Mishima, Machida, Japan

[73] Assignee: Research Development Corp. of Japan, Tokyo, Japan

[21] Appl. No.: 890,558

[22] Filed: Jul. 30, 1986

[30] Foreign Application Priority Data

Aug. 6, 1985 [JP] Japan .................................. 60-171760

[51] Int. Cl.$^4$ ............................ C08J 9/28; B01J 13/02
[52] U.S. Cl. .................................. 521/62; 210/500.21; 210/502.1; 210/692; 521/63; 521/64; 521/56
[58] Field of Search ................ 210/500.21, 502.1, 692; 521/62, 64, 63

[56] References Cited

U.S. PATENT DOCUMENTS

| | | | |
|---|---|---|---|
| 3,244,772 | 4/1966 | Von Bonin | 521/64 |
| 3,255,127 | 6/1966 | Von Bonin | 521/62 |
| 3,442,842 | 7/1966 | Von Bonin | 521/64 |
| 4,137,380 | 1/1979 | Gunning et al. | 521/62 |
| 4,461,849 | 7/1984 | Karickhoff | 521/63 |

Primary Examiner—Morton Foelak
Attorney, Agent, or Firm—Stephen F. K. Yee

[57] ABSTRACT

A urea adsorbent and a method for its production are disclosed, the adsorbent comprising hollow microspheres each having an outer layer formed of a urea-permeable polymer and an inner layer formed of a polymer containing a polyoxyalkylene glycol derivative expressed by the following formula:

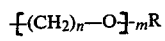

wherein R stands for hydrogen or a methyl group and n is an integer of 2–5 and m is an integer of at least 3. The adsorbent can selectively adsorb urea with a high adsorbing activity and does not interact with other substances than urea and, therefore, is useful as an artificial kidney.

The adsorbent may be prepared by subjecting a w/o/w type emulsion to polymerization wherein a radical polymerizable polyoxyalkylene glycol derivative is dissolved in the inner aqueous phase of the emulsion and an oil-soluble radical polymerizable monomer is used as the outer oil phase.

7 Claims, 1 Drawing Figure ( X 200 )

METHOD OF PREPARING UREA ADSORBENT

BACKGROUND OF THE INVENTION

1. Field of the Invention:

This invention relates generally to a urea adsorbent and, more particularly, to a novel polymer-based urea adsorbent suitable for use as an artificial kidney.

2. Description of the Prior Art:

Artificial kidneys currently used include those of a dialysis type, filtration type, adsorption type and enzyme-fixation type. While these known artificial kidneys have certain merits, they suffer from some drawbacks too. Thus, there have not been developed yet artificial kidneys satisfactorily used for chronic or acute kidney troubles.

For example, an artificial kidney of a dialysis type, which is now most widely used, constantly requires a fresh dialysate. Further, the artificial kidney of this type is generally large in size and is inconvenient because patients are inevitably restrained in a hospital for a long time.

An artificial kidney of a filtration type has a great drawback because serum containing useful components is discarded together with effete matters.

An artificial kidney of an enzyme-fixation type, which is recently developed rapidly, has a problem of the inactivation of the enzyme at or after the fixation of urease. In addition, its performance is susceptible to environment conditions such as temperature and acidity.

An artificial kidney of an adsorption type is convenient because it is small in size and light in weight. However, the adsorbent, generally activated carbon, is not effective for the adsorption of urea which is a main ingredient secreted in urine, though it effectively adsorbs organic effete or waste matters.

At present, it has become an important problem to develop a urea-removing substance for use in an artificial kidney of an adsorption type. Oxystarch (Kobunshi Ronbunshu 39, 629) and a product obtained by reaction of a hydrazide-containing polymer with formaldehyde or glyoxal (Publication of Unexamined Japanese Patent Application No. 69489/1976) have been proposed as such an adsorbent but are not satisfactory in practice.

SUMMARY OF THE INVENTION

The present inventor has made an extensive study on selective urea adsorbent for the purpose of solving the above-mentioned problems and has found that a specific polyoxyalkylene glycol derivative is useful as a urea adsorbent. In accordance with the present invention there is provided a urea adsorbent comprising hollow microspheres each including an outer layer formed of a urea-permeable polymer, and an inner layer formed of a polymer containing, as its component, a polyoxyalkylene glycol derivative expressed by the following formula (I):

$$-\!\!\!+\!\!(CH_2)_n\!-\!\!O\!\!+\!\!_m R \qquad (I)$$

wherein n is an integer of 2–5, m is an integer of at least 3 and R stands for hydrogen or a methyl group.

The method for the preparation of the urea adsorbent according to the present invention is not specifically limited. However, an emulsion polymerization method is preferable because of the ease and simplicity simpleness of the preparation steps. Especially, a w/o/w type emulsion method using a radical polymerizable polyoxyalkylene glycol derivative of the formula (II) or (III):

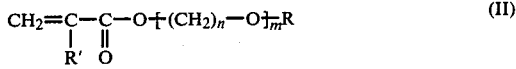

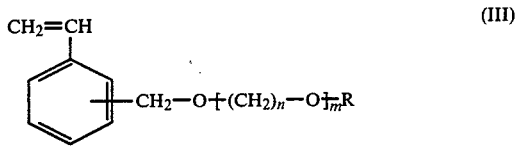

wherein n is an integer of 2–5, m is an integer of at least 3, R stands for hydrogen or methyl group and R' stands for hydrogen or a hydrocarbon group having 1–10 carbon atoms, is most preferable.

The urea adsorbent in the form of hollow microspheres may be suitable obtained by emulsion polymerization of a w/o/w type emulsion in which the radical polymerizable polyoxyalkylene glycol derivative of the formula (II) or (III) is dissolved in the inner aqueous phase and an oil soluble radical polymerizable monomer is used as the oil phase.

During the course of the polymerization, the polyoxyalkylene glycol derivative of the general formula (II) or (III) is co-polymerized with the oil soluble radical polymerizable monomer. Since the radical polymerizable polyoxyalkylene glycol derivative is dissolved in the inner aqueous phase of the w/o/w type emulsion, the resulting hollow microspheres each have an inner layer formed of a polymer mainly composed of the radical polymerizable polyoxyalkylene glycol derivative of the formula (II) or (III) and an outer layer formed of a polymer composed mainly of the oil soluble radical polymerizable monomer. The outer layer may be other polymer than the polymer of the oil soluble radical polymerizable monomer as long as the outer layer permits the permeation of urea therethrough.

A polyoxyalkylene glycol derivative generally has a property to interact with and adsorb (remove) useful components in human bodies, such as vitamin B-12 and polypeptides, besides waste matters. To prevent the removal, by adsorption, of the useful components in human bodies, it is effective to reduce the contact between the useful components and the polyoxyalkylene glycol derivative. This can be achieved by the use of the hollow microspheres with the above-described structure. As described previously, the outer layer of the hollow microspheres is formed of an urea permeable polymer such as a polymer of an oil soluble radical polymerizable monomer. The outer layer serves as a separating membrane.

That is, due to the molecular sieve effect of the membrane (outer layer), high molecular weight and middle molecular weight substances which are effective components in human bodies cannot pass therethrough, permitting the passage of low molecular weight substances such as water, urea, metal ion, therethrough. The low molecular weight substances, after passage through the outer layer, are then brought into contact with the inner layer of the polyoxyalkylene glycol derivative and urea is selectively adsorbed thereby.

The method of the preparation of the urea adsorbent is described below. A mixture containing an oil soluble radical polymerizable monomer, a nonionic surfactant, a radical polymerization initiator and, if necessary, a crosslinking agent is mixed with an aqueous solution containing a radical polymerizable polyoxyalkylene glycol derivative of the formula (II) or (III) and the mixture is vigorously agitated to form a w/o emulsion. The w/o emulsion is then added into water containing a cationic or anionic surfactant with stirring to form a w/o/w emulsion. The w/o/w emulsion is then heated with stirring under nitrogen atmosphere to effect the polymerization. The stirring is conducted at a rotational speed so that the w/o/w emulsion is not destroyed, preferably at a rotational speed of 100-300 r.p.m.

The nonionic surfactant may include, for example, polyoxyethylene oleyl ether, polyoxyethylene nonylphenyl ether, polyoxyethylene sorbitan trioleate, polyoxyethylene sorbitan monooleate, or polyoxyethylene glycerin monostearate. The amount of the noionic surfactant used varies with the amount of the radical polymerizable polyoxyalkylene glycol derivative of the formula (II) or (III). Since the compound of the formula (II) or (III) has a property as a nonionic surfactant, the above-described nonionic surfactant is used only when otherwise a stable w/o/w emulsion is not obtainable, in a minimum required amount.

The anionic surfactant may include, for example, sodium laurylsulfate, sodium cetylsulfate, sodium dodecylbenzenesulfonate, sodium laurolylsarcosine or sodium polyoxyethylene lauryl ether phosphate. These anionic surfactants may be used singly or in combination of two or more.

The cationic surfactant may include, for example, cetylpyridinium chloride, benzalkonium chloride, or cetyltrimethylammohium chloride. These cationic surfactants may be used singly or in combination of two or more. If desired, inorganic salts(e.g. sodium hexametaphosphate) may be used in conjunction with the above anionic or cationic surfactant.

As a result of the polymerization of the oil soluble radical polymerizable monomer and the radical polymerizable polyoxyalkylene glycol derivative of the formula (II) or (III), hollow microspheres having an outer, urea-permeable layer formed of a polymer composed mainly of the oil soluble radical polymerizable monomer and an inner layer formed of a polymer containing, as its component, a polymer of the polyoxyalkylene glycol derivative of the formula (II) or (III) crosslinked with the polymer of the outer layer.

The thus obtained microspheres are separated from the reaction mixture by sedimentation, centrifugation, vacuum filtration, pressurized filtration, or so on. The separated microspheres are washed with water and then with methanol and dried by hot air or in vacuum. The resulting microspheres have a size of 2-100 $\mu$m and a high mechanical strength. Further, the microspheres are stable in air and under dried conditions so that the microspheres withstand long-period storage. The microspheres have a hollow structure with a wall thickness of about 1-10 $\mu$m. The hollow structure may be confirmed by photomicroscopy after crushing the microspheres.

It is deduced from the below-described facts that the hollow microspheres thus obtained have an outer layer formed of a polymer composed mainly of the oil soluble radical polymerizable monomer and an inner layer formed of a polymer containing the polyoxyalkylene glycol derivative crosslinked with the polymer of the outer layer. Thus, the adsorbent according to the present invention is prepared by w/o/w type emulsion polymerization, in which the outer oil phase contains the oil soluble radical polymerizable monomer and the inner aqueous phase contains the radical polymerizable polyoxyalkylene glycol derivative of the formula (II) or (III). The fact that the polyoxyalkylene glycol derivative is contained in the inner layer which does not contact directly with the useful substances in human bodies is also deduced by the fact that, while microspheres (Comparative Example 2) formed from a polyethylene glycol and a crosslinking agent by a method disclosed in Publication of Unexamined Japanese Patent Application No.55009/1985 interact with vitamins or hormones, the hollow microspheres according to the present invention do not interact with such vitamins and hormones.

The hollow fine microspheres as such may be used as a urea adsorbent. It is possible to modify them for imparting hydrophilicity thereto or to subjecting them to a hydrophilic polymer coating treatment or plasma treatment before using them as a urea adsorbent.

Illustrative of suitable radical polymerizable polyoxyalkylene glycol derivatives expressed by the general formula (II) are polyoxyethylene glycol mono(metha)acrylate, polyoxytrimethylene glycol mono(metha)acrylate, polyoxytetramethylene glycol mono(metha) acrylate, $\omega$-methoxylpolyoxyethylene glycol mono(metha)acrylate, $\omega$-methoxypolyoxytrimethylene glycol mono(metha)acrylate, and $\omega$-methoxypolyoxytetramethylene glycol mono(metha)acrylate. Illustrative of suitable radical polymerizable polyoxyalkylene glycol derivatives expressed by the general formula (III) are $\alpha$-(p-vinylbenzyloxy)-polyoxyethylene glycol, $\alpha$-(p-vinylbenzyloxy)-polyoxytrimethylene glycol, $\alpha$-(p-vinylbenzyloxy)-polytetramethylene glycol, $\alpha$-(p-vinylbenzyloxy)-$\omega$-methoxypolyoxyethylene glycol, $\alpha$-(p-vinylbenzyloxy)-$\omega$-methoxypolyoxytrimethylene glycol and $\alpha$-(p-vinylbenzyloxy)-$\omega$-methoxypolyoxytetramethylene glycol.

Examples of the polymers containing as their component a polyoxyalkylene glycol derivative of the formula (I) include a copolymer of ethyl methacrylate/polyoxyethylene glycol dimethacrylate (number average molecular weight: 400)/polyoxyethylene glycol monomethacrylate, a copolymer of styrene/ethylene glycol dimethacrylate/$\omega$-methoxypolyoxyethylene glycol monomethacrylate, a copolymer of ethyl methacrylate/polyoxyethylene glycol dimethacrylate/$\alpha$-(p-vinylbenzyloxy)polyoxyethylene glycol, and a copolymer of methyl methacrylate/divinylbenzene/$\alpha$-(p-vinylbenzyloxy)-$\omega$-methoxypolyoxyethylene glycol. The hollow microsphere adsorbent of the present invention is composed of the above-exemplified polymer and has an outer layer formed of a urea-permeable polymer composed mainly of an oil soluble monomer such as ethyl methacrylate or styrene and an inner layer formed of a polymer composed mainly of a radical polymerizable polyoxyalkylene glycol derivative expressed by the general formula (II) or (III).

The radical polymerizable polyoxyalkylene glycol derivative of the formula (II) or (III) may be produced by any known method. For example, the derivative of the formula (II) in which the terminal group is hydrogen may be obtained by adding an alkylene oxide to a hydroxyalkyl acrylate in the presence of stannic chloride, as disclosed in Japanese Patent Publication No. 15493/1978. In the case of the derivative of the formula (II) in which the terminal group is methyl may be prepared by the transesterification of an acrylate with a polyoxyalkylene glycol whose one terminal hydroxyl group is substituted by a methoxy group (Kobunshi Ronbunshu 39, 165).

The radical polymerizable polyoxyalkylene glycol derivative of the formula (III) may be obtained by reacting a corresponding polyoxyalkylene glycol with sodium hydroxide to form a sodium salt, followed by the reaction with chloromethylstyrene (Publication of Unexamined Japanese Patent Application No. 121730/1978). The thus synthesized polyoxyalkylene glycol derivative of the formula (II) or (III) may be used singly or in combination of two or more.

The number average molecular weight of the polyoxyalkylene glycol derivative of the formula (II) or (III) is generally 120–50000, preferable 200–10000. A number average molecular weight of less than 120 is insufficient to impart appreciable urea adsorbing properties to the resulting polymer of the general formula (I). Further, the glycol derivative with such too low a molecular weight becomes poor in hydrophilicity so that it becomes difficult to dissolve the glycol derivative in the inner aqueous phase of the w/o/w type emulsion, especially when polyoxytetramethylene glycol derivative is employed as the alkylene glycol of the formula (II) or (III). On the other hand, if the number average molecular weight is greater than 50000, the urea absorbing power of the polymer tends to be lowered and the mechanical strength of the microspheres becomes low.

The amount of the polyoxyalkylene glycol derivative of the formula (II) or (III) used is preferably 1–50 weight % based on the oil soluble monomer. Too small an amount causes insufficient urea absorbing power while too large an amount fails to produce microspheres with desired structure.

As described above, the terminal group of the polyoxyalkylene glycol derivative of the formula (II) or (III) is hydrogen or methyl. Generally, in an artificial kidney, the control the concentration of potassium and sodium ion is one of the important problem. A great difference exists in the ion adsorbing power between the hydrogen-terminated polyoxyethylene glycol derivative and the methyl-terminated polyoxyethylene glycol derivative, i.e. the former glycol derivative has a greater adsorbing power. By converting a portion of the terminal hydrogen into methyl, however, it is possible to obtain microspherical adsorbent having a desired ion adsorbing power.

The oil soluble radical polymerizable monomer is not specifically limited in the present invention. Illustrative of suitable monomers are aromatic radical polymerizable monomers such as styrene, α-methylstyrene, β-methylstyrene, and p-vinyltoluene; ester type radical polymerizable monomers such as methyl acrylate, methyl methacrylate, ethyl acrylate, ethyl methacrylate, propyl acrylate, propyl methacrylate, butyl acrylate, butyl methacrylate and methyl α-ethylacrylate; and vinyl type radical polymerizable monomers such as vinyl chloride, vinyl acetate and methyl vinyl ether. These oil soluble polymerizable monomers may be used singly or in combination of two or more.

A crosslinking agent may be used, if desired. Examples of the crosslinking agents include divinylbenzene, ethylene glycol dimethacrylate, polyoxyethylene glycol dimethacrylate, polydimethylsiloxane dimethacrylate, polyamide dimethacrylate. The amount of the crosslinking agent is 0–50 wt % based on the oil soluble radical polymerizable monomer. An amount of the crosslinking agent over 50 wt % is undesirable because of the lowering of the permeation rate of water and urea of the hollow microspherical adsorbent.

The microspherical adsorbent produced by w/o/w type emulsion polymerization and formed of a polymer containing as its component a polyoxyalkylene glycol derivative of the general formula (I) should allow the passage of water and urea in a facilitated manner. For this reason, it is preferable to use an ester-type radical polymerizable monomer capable of providing a polymer of a high permeability such as methyl acrylate, methyl methacrylate, ethyl acrylate or ethyl methacrylate and to use polyoxyethylene glycol dimethacrylate as a crosslinking agent. When chloromethylstyrene, which is hydrophobic in nature, is used as the radical polymerizable monomer, it is effective to convert its polymerization product into an ammonium salt so as to impart hydrophilicity thereto. It is also effective to use glycidyl methacrylate as the radical polymerizable monomer and to react, after the radical polymerization, the polymerized product with a nucleophile so as to impart hydrophilicity by opening the three membered rings.

Illustrative of suitable radical polymerization initiators are peroxides such as cumene hydroperoxide, dicumylperoxide, benzoylperoxide and lauroylperoxide; azobis-type initiators such as azobisisobutyronitrile and azobis-2,4-dimethylvaleronitrile; and redox initiators such as a combination of peroxodisulfate and sodium hydrogen sulfite. Both water soluble and oil soluble polymerization initiators may be used for the purpose of the present invention.

The urea adsorbent obtained in the foregoing manner has a potent urea adsorbing property. For example, when 0.5 g of the urea adsorbent is immersed in 50 ml of an aqueous urea solution having a urea concentration of 100 mg/dl for 1 hour, the urea concentration is decreased to about half. In addition, the urea adsorbent is advantageous because the adsorbent having adsorbed urea may be regenerated by washing with hot water for the desorption of the urea, followed by filtration and drying.

BREIF DESCRIPTION OF DRAWING

In the drawing, the sole FIGURE is a microphotograph showing the structure of microspherical adsorbent according to the present invention.

DESCRIPTION OF THE PREFERRED EMBODIMENTS

Figure 1:
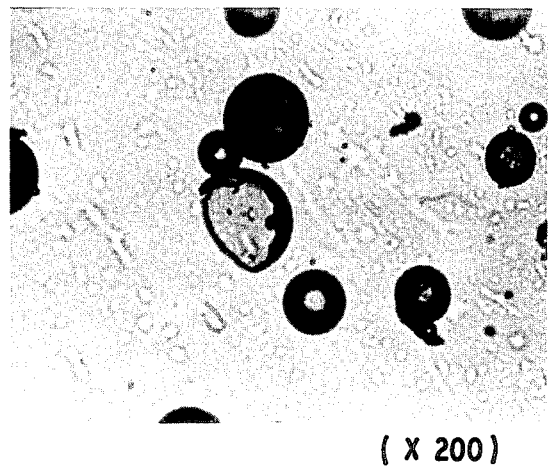

The present invention will now be described in detail below by way of examples. It is to be understood, however, that these examples are not to be considered as limitting the scope of the invention.

EXAMPLE 1

Into a mixture containing 19 g of ethylmethacrylate, 2 g of tetraethylene glycol dimethacrylate [NK Ester 4G (trademark) manufactured by SHIN-NAKAMURA CHEMICAL Co., LTD.], 2 g of sorbitan monooleate and 0.01 g of azobisisobutyronitrile were added 10 ml of an aqueous solution containing 2 g of polyoxyethylene glycol monomethacrylate and the resulting mixture was vigorously stirred to obtain a w/o type emulsion.

To a four-necked flask equipped with a stirring bar, a condenser, a tap funnel and a nitrogen feed pipe were charged 1 g of sodium dodecylsulfate, 2.5 g of sodium hexametaphosphate and 450 ml of water and the mixture was heated to 70° C. while introducing nitrogen gas. Then the above w/o type emulsion was added, dropwise from the tap funnel, into the flask at 70° C. with stirring. After the addition of the w/o type emulsion, the mixture within the flask was reacted at 80° C. and at a stirring rate of 300 r.p.m. for 5 hours. The precipitate formed by the polymerization was recovered by filtration under vacuo, washed five times with water and thrice with methanol, and dried under a reduced pressure to obtain hollow microspheres each having an outer layer formed of a copolymer composed mainly of ethyl methacrylate and tetraethyelene glycol dimethacrylate and an inner layer formed of a copolymer composed mainly of polyoxyethyelene glycol monomethacrylate and tetraethylene glycol dimethacrylate and crosslinked with the copolymer of the outer layer.

The hollow microspheres were found to have an average size of 100 $\mu$m and a wall thickness of about 2 $\mu$m. The hollow structure was confirmed by optical microscope (Optiphoto XF-BD manufactured by Nikon Inc.) after crushing the sample microspheres. FIG. 1 is a microphotograph of the microspheres according to the present invention, in which a broken microsphere appears at the center and unbroken microspheres appear therearound. The hollow microspheres are insoluble in water and in usual organic solvents. The microspheres have good dispersibility in water.

The hollow microspheres as such were used as urea adsorbent to measure the amount of urea adsorbed thereby in the following manner: To an aqueous solution (50 ml) containing 100 mg/dl of urea were added 0.5 g of the adsorbent and the mixture was agitated at 37° C. for 2 hours and centrifuged. The supernatant thus obtained was recovered and colorimetrically analyzed to determine the concentration of urea according to the diacetyl method using a spectrophotometer (150-20 type manufactured by Hitachi Ltd.; wavelength: 480 nm). As a result, the concentration of urea was found to decrease to 60 mg/dl. For the purpose of comparison, a similar test was conducted using activated carbon in place of the hollow microspheres, revealing that the urea concentration was reduced to 95 mg/dl.

The foregoing results indicate that the urea absorbent according to the present invention which is composed of a polymer containing polyoxyethyelne glycol as its component has an excellent urea adsorbing property.

EXAMPLE 2

Into a mixture containing 19 g of ethyl methacrylate, 1 g of ethylene glycol dimethacrylate, 2 g of sorbitan monooleate and 0.01 g of azobisisobutyronitrile were added 10 ml of an aqueous solution containing 2 g of methoxy-terminated polyoxyethylene glycol monomethacrylate [NK Ester-M-230G (number aaverage molecular weight: ca. 1000) manufactured by SHIN-NAKAMURA CHEMICAL Co., LTD.] to obtain a w/o type emulsion. The emulsion was reacted in the same manner as Example 1 to obtain hollow microspheres formed of a polymer containing methoxyterminated polyoxyethylene glycol as its component. Each microsphere has an outer layer formed of a copolymer composed mainly of ethyl methacrylate and ethylene glycol dimethacrylate and an inner layer formed copolymer composed mainly of methoxy-terminated polyoxyethylene monomethacrylate. The microspheres were found to have an average size of 70 $\mu$m and a wall thickness of 3 $\mu$m. The hollow structure was confirmed by optical microscope in the same manner as in Example 1. The microspheres were found to be insoluble in water and in usual organic solvents and have good dispersability in water. The microspheres were tested for adsorbing property in the same manner as in Example 1, revealing that the concentration of urea of the aqueous urea solution after the treatment with the microspheres was reduced to 80 mg/dl. The urea adsorbing property of the microspheres of Example 2 is thus inferior to that of the microspheres of Example 1 but is far superior in comparison with activated carbon.

EXAMPLE 3

Into a mixture containing 19 g of ethyl methacrylate, 1 g of ethylene glycol dimethacrylate, 2 g of sorbitan monooleate and 0.01 g of azobisisobutyronitrile were added 10 ml of an aqueous solution containing 2 g of mono(p-vinylbenzyloxy)tetraoxyethylene glycol to obtain a w/o type emulsion. The emulsion was reacted in the same manner as Example 1 to obtain hollow microspheres formed of a polymer containing hydroxyl-terminated polyoxyethylene glycol as its component. Each microsphere has an outer layer formed of a copolymer composed mainly of ethyl methacrylate and ethylene glycol dimethacrylate and an inner layer formed of a copolymer composed mainly of mono(p-vinylbenzyloxy)tetraoxyethyelene glycol. The microspheres were found to have an average size of 45 $\mu$m and a wall thickness of 3.5 $\mu$m and to be insoluble in water and in usual organic solvents and good in dispersability in water. The hollow structure was confirmed by optical microscope. The urea adsorbing property of the microspheres was tested in the same manner as in Example 1, revealing that the concentration of urea of the aqueous solution after the treatment with the microspheres was reduced to 70 mg/dl. The microspherical adsorbent according to the present invention exhibits a high urea adsorbing power even if the molecular weight of the polyoxyethylene glycol is relatively small. Comparative Example 1

Into a mixture containing 19 g of ethyl methacrylate, 1 g of ethylene glycol dimethacrylate, 5 g of sorbitan monooleate and 0.01 g of azobisisobutyronitrile were added 10 ml of water to obtain a w/o type emulsion. The emulsion was reacted in the same manner as Example 1 to obtain hollow microspheres having an average size of 50 $\mu$m and a wall thickness of 5 $\mu$m. The hollow structure was confirmed by optical microscope. The microspheres were composed of a copolymer of ethyl methacrylate and ethylene glycol dimethacrylate and did not contain a polyoxyalkylene glycol derivative. Using the thus obtained microspheres as an adsorbent, a urea adsorbing test was carried out in the same manner as in Example 1 to reveal that the urea concentration of the aqueous urea solution after the treatment was 100 mg/dl and the microspheres had no urea adsorbing property. The foregoing results suggest that the presence of a polyoxy- alkylene glycol derivative is essential for adsorption of urea.

COMPARATIVE EXAMPLE 2

In 50 ml of methyl ethyl ketone were dissolved 37.5 g of polyoxyethylene glycol monomethacrylate with a number average molecular weight of 400 (Blenmer PE350 manufactured by Nippon Oil and Fats Co., Ltd.), 12.5 g of ethylene glycol dimethacrylate and 0.1 g of azobisisobutyronitrile to form a first solution. On the other hand, 15 g of sodium chloride and 10 g of polyvinyl alcohol were dissolved in 500 ml of water to give a second solution. The first solution was then added into the second solution which was previously heated to 70° C., and the mixture was agitated to form a suspension. The suspension was allowed to react for 10 hours. The precipitates formed by the polymerization were collected by means of a glass filter, washed thrice with water and thrice with acetone and dried under vacuum to obtain microspheres with an average size of 30 μm. The microspheres had no hollow structure and were formed of a copolymer of polyoxyethylene glycol monomethacrylate and ethyelene glycol dimethacrylate. Using the microspheres as an adsorbent, a urea adsorbing test was carried out in the same manner as described in Example 1 to reveal that the concentration of urea in the aqueous urea solution was decreased to 70 mg/dl.

The microspheres were then tested for adsorption of creatinine (aqueous solution with a concentration of 10 μg/ml), albumin (aqueous solution with a concentration of 100 μg/ml) and vitamin B-12 (aqueous solution with a concentration of 10 μg/ml). The tests were conducted in the same manner as in urea adsorption test by adding 0.5 g of the microspheres in 50 ml of each of the above aqueous solutions and agitating the mixture at 37° C. for 2 hours. The mixture was then centrifuged to recover a supernatant. Each supernatant was subjected to colorimetric analysis. The maximum absorption wavelengths of the creatinine, albumin and vitamin B-12 aqueous solutions are 234, 279 and 550 nm, respectively. By the treatment of the microspheres, the maximum absorption wavelengths of the creatinine and albumin solutions were shifted to 225 and 275 nm, respectively. No change was observed in the case of the vitamin B-12 aqueous solution. The above results indicate that some change occurred in creatinine and albumin upon the treatment with the microspheres.

Similar tests were carried out using the hollow microspheres obtained in Examples 1-3. No changes in concentration or in maximum absorption wavelengths were observed on the creatinine, albumin and vitamin B-12 solutions treated with the hollow microspheres.

The foregoing results suggest that microspheres whose surfaces are formed of a polyoxyalkylene glycol derivative interact not only with urea but also with other ingredients and give undesirable results. In contrast, with the hollow microspheres having an outer layer formed of a urea-permeable polymer composed mainly of an oil soluble radical polymerizable monomer and an inner layer formed of a polymer composed mainly of a polyoxyalkylene glycol derivative, the undesirable interaction between the latter polymer and the ingredients other than urea can be effectively prevented and urea alone can be selectively adsorbed.

The urea adsorbent according to the present invention has an excellent urea adsorbing power and can selectively adsorb urea. Thus, the adsorbent is suitably utilized as an artificial kidney.

What is claimed is:

1. A method of preparing a urea adsorbent comprising hollow microspheres each including an outer layer formed of a urea-permeable polymer, and an inner layer formed of a polymer containing, as its component, a polyoxyalkylene glycol derivative expressed by the following formula (I)

wherein n is an integer of 2-5, m is an integer of at least 3 and R stands for hydrogen or a methyl group, said method comprising subjecting a w/o/w type emulsion to radical polymerization, wherein a radical polymerizable polyoxyalkylene glycol derivative represented by the formula (II) or (III):

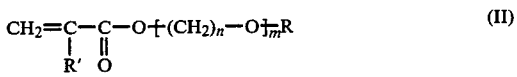

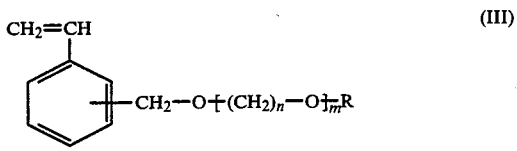

wherein n is an integer of 2-5, m is an integer of at least 3, R stands for hydrogen or a methyl group and R′ stands for hydrogen or a hydrocarbon group having 1-10 carbon atoms, is dissolved in the inner phase of said w/o/w type emulsion and an oil-soluble radical polymerizable monomer is used as the oil phase of said w/o/w type emulsion.

2. A method as set forth in claim 1, wherein said ureapermeable polymer is a polymer of an oil-soluble, radical polymerizable monomer.

3. A method as set forth in claim 2, wherein said polymer of an oil-soluble, radical polymerizable monomer is a copolymer of ethylmethacrylate and tetraethylene glycol dimethacrylate or a copolymer of ethylmethacrylate and ethylene glycol dimethacrylate.

4. A method as set forth in claim 1, wherein said polymer containing, as its components, a polyoxyalkylene glycol derivative is a copolymer of polyoxyethylene monomethacrylate and tetraethylene glycol dimethacrylate, a copolymer of polyoxyethylene glycol monomethacrylate and methoxy-terminated polyoxyethylene glycol monomethacrylate, or a copolymer of polyoxyethylene glycol monomethacrylate and mono(p-vinylbenzyloxy)tetraoxyethylene glycol.

5. A method as set forth in claim 1, wherein the number average molecular weight of said polyoxyalkylene glycol derivative is in the range of 120-50000.

6. A method as set forth in claim 1, wherein said hollow microspheres have an average size of 2-100 μm and a wall thickness of 1-10 μm.

7. A method as set forth in claim 1, further including the addition of a crosslinking agent in the amount of 0-50 wt. % of said oil-soluble radical polymerizable monomer.

* * * * *